(12) United States Patent
Quehl et al.

(10) Patent No.: US 12,398,431 B2
(45) Date of Patent: Aug. 26, 2025

(54) OLIGONUCLEOTIDE PROBE FOR THE SPECIFIC DETECTION OF MICROORGANISMS, CORRESPONDING METHOD AND USE

(71) Applicant: Testo bioAnalytics GmbH, Titisee-Neustadt (DE)

(72) Inventors: Paul Quehl, Gottingen (DE); Zinaida Vasileuskaya-Schulz, Freiburg (DE); Stefanie Boos, Villingen-Schwenningen (DE)

(73) Assignee: Testo bioAnalytics GmbH, Titisee-Neustadt (DE)

( * ) Notice: Subject to any disclaimer, the term of this patent is extended or adjusted under 35 U.S.C. 154(b) by 227 days.

(21) Appl. No.: 17/174,799

(22) Filed: Feb. 12, 2021

(65) Prior Publication Data
US 2021/0310081 A1    Oct. 7, 2021

(30) Foreign Application Priority Data
Feb. 14, 2020    (DE) .......................... 102020103958.1

(51) Int. Cl.
*C12Q 1/6888*    (2018.01)
*C12Q 1/6841*    (2018.01)
*G01N 21/64*     (2006.01)

(52) U.S. Cl.
CPC ......... *C12Q 1/6888* (2013.01); *C12Q 1/6841* (2013.01); *G01N 21/6428* (2013.01); *C12Q 2600/158* (2013.01); *G01N 2021/6439* (2013.01)

(58) Field of Classification Search
CPC ............... C12Q 1/6888; C12Q 1/6841; C12Q 2600/158; C12Q 1/6818; C12Q 1/689; G01N 21/6428; G01N 2021/6439
See application file for complete search history.

(56) References Cited

U.S. PATENT DOCUMENTS

2019/0078147 A1 *    3/2019    Powell ................. C12Q 1/6818

FOREIGN PATENT DOCUMENTS

| EP | 0745690 A2 | 12/1996 | |
| WO | 0065093 A2 | 11/2000 | |
| WO | 02006531 | 1/2002 | |
| WO | WO-2008021446 A2 * | 2/2008 | ........... C12Q 1/6818 |

OTHER PUBLICATIONS

Mach (Analyst (2019) vol. 144, pp. 1565-1574) E pub Jan. 10, 2019).*
Silverman (Trends in Biotechnology (2005) vol. 23, pp. 225-230).*
Wu(Biosensors and Bioelectronics 26 (2010) 491-496).*
Didenko (Biotechniques. Nov. 2001 ; 31(5): 1106-1121).*
Mach, K. E. et al. "Optimizing peptide nucleic acid probes for hybridization-based detection and identification of bacterial pathogens" (2019) Analyst 144: 1565-1574.
Cao, H. T. et al. "Effectiveness of hairpin probe in increasing the limit of detection for gold nanowire based-biosensor" (2014) Advances in Natural Sciences: Nanoscience and Nanotechnology 5: 045017 (6pp).
Tam-Chang, S. W. et al. "Stem-loop probe with universal reporter for sensing unlabeled nucleic acids" (2007) Analytical Biochemistry 366: 126-130.
Han, S. X. et al. "Molecular Beacons: A Novel Optical Diagnostic Tool" (2013) Arch. Immunol. Ther. Exp. 61: 139-148.

* cited by examiner

*Primary Examiner* — Cynthia B Wilder
(74) *Attorney, Agent, or Firm* — Volpe Koenig

(57) ABSTRACT

An oligonucleotide probe combination (1) for the specific detection of microorganisms having a primary probe (5) and a secondary probe (6), wherein the primary probe (5) has at least one functional section (2) and the secondary probe (6) at least one tag (3) generating a detectable signal. The functional section (2) binds specifically to a target sequence of a microorganism to be detected, and the primary probe (5) and the secondary probe (6) are linked to one another but constitute separate chains (8).

10 Claims, 3 Drawing Sheets
Specification includes a Sequence Listing.

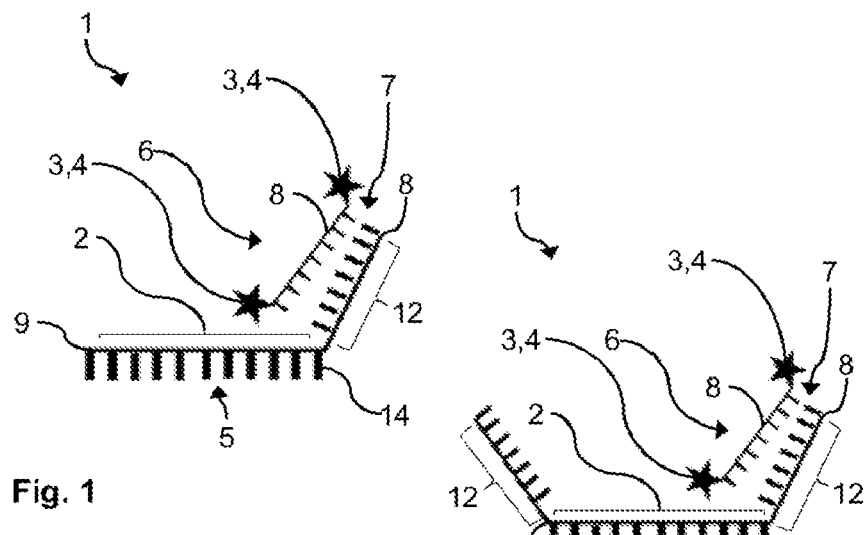
Fig. 1
Fig. 2
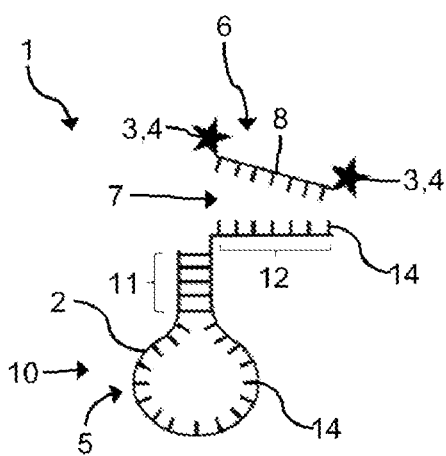
Fig. 3
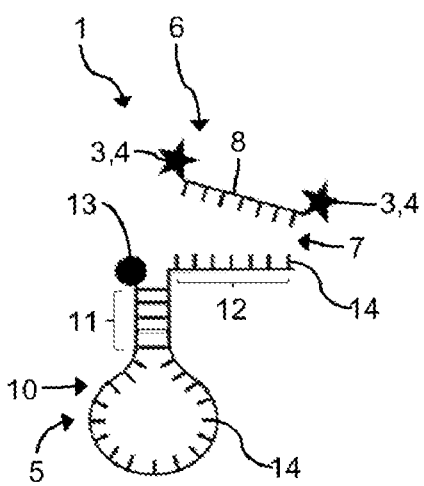
Fig. 4

Fig. 7

| Secondary probe name | Sequence (probe) | Length (bp) | Comment |
|---|---|---|---|
| SQ1 | TCCATCCCTCCCTCCACTCTCTTTT | 25 | |
| SQ1L | TCCATCCCTCCCTCCACTCTCTTTT | 25 | With LNAs |
| SQ2 | TTTTCCTCCCTCCCTCCCTCCTTTT | 25 | |
| SQ3 | AAAAGGAGGGAGGGAGGGAGGAAAA | 25 | |
| SQ4 | AAAGAGAGGGGGAGAGAAA | 20 | |
| SQ4L | TTTTCTCCCCTCTCTTTT | 19 | Only possible with LNAs (doubly underlined) |
| SQ5 | TTTTCCCTTCCCTTTT | 16 | Only possible with LNAs (doubly underlined) |
| SQ6 | AAAAGGGAGGGAAAA | 15 | Only possible with LNAs (doubly underlined) weak RNA binding |
| SQ7 | AAGGGAGGGGAGGGAA | 17 | |
| SQ8 | AAGGGGGGGGGAA | 13 | With LNAs, normal binding to RNA (homopurine) |

Fig. 8

| Primary probe name | Sequence (probe) |
|---|---|
| Q162-3' (with internal hairpin) | cccgggtCCTACTTCTTTTGCAACCCACTaccccgAAAAGGAGGGAGGGAGGGAGGAAAA |
| Q162-3' (with internal hairpin and bait 5' and 3') | AAAAGGAGGGAGGGAGGGAGGAAAAcccgggtCCTACTTCTTTTGCAACCCACTacccggAAAAGGAGGGAGGGAGGGAGGAAAA |
| L162-3' (linear probe) | CCTACTTCTTTTGCAACCCACTAAAAGGAGGGAGGGAGGGAGGAAAA |
| RL162 (linear probe at 5' and 3') | AAAAGGAGGGAGGGAGGGAGGAAAACCTACTTCTTTTGCAACCCACTAAAAGGAGGGAGGGAGGGAGGAAAA |
| RLV162 (linear probe at 5' and 3' with a linker base) | AAAAGGAGGGAGGGAGGGAGGAAAAtCCTACTTCTTTTGCAACCCACTAAAAGGAGGGAGGGAGGGAGGAAAA |

OLIGONUCLEOTIDE PROBE FOR THE SPECIFIC DETECTION OF MICROORGANISMS, CORRESPONDING METHOD AND USE

INCORPORATION BY REFERENCE

German Patent Application No. 10 2020 103 958.1, filed Feb. 14, 2020, is incorporated herein by reference as if fully set forth.

The Sequence Listing filed Jun. 23, 2021, created Jun. 23, 2021, titled "Sequence Listing," and having a file size of 3,586 bytes is incorporated herein as if fully set forth.

The Sequence Listing filed Apr. 6, 2023, created Mar. 31, 2023, titled "Substitute Sequence Listing," and having a file size of 3,978 bytes is incorporated herein as if fully set forth.

TECHNICAL FIELD

The invention relates to an oligonucleotide probe combination for the specific detection of microorganisms, in particular for the detection of at least one target sequence, having at least one functional section and at least one detectable tag, in particular a color tag, wherein the at least one functional section binds specifically to the target sequence of microorganisms of the group to be detected and triggers a detectable signal through an interaction with the at least one tag.

BACKGROUND

Known methods for the specific detection of nucleic acids, i.e. DNA and/or RNA molecules, in individual cells include for example in-situ hybridization (ISH). This involves using short synthetic nucleic acid probes that bind to the target sequence to be detected via complementary base pairings. A variant of ISH technology in which the nucleic acid probes are labeled with fluorescent tags is fluorescence in-situ hybridization (FISH).

In the known FISH methods, the cell envelope of the microorganisms present in the sample is rendered permeable for nucleic acid probes. The nucleic acid probes, which consist of an oligonucleotide and a label bound thereto, can then penetrate the cell envelope and bind to the target sequence in the cell interior. Additional fixing results in the cell structure being maintained.

Because of the sequence-dependent, high variability of the physicochemical properties of oligonucleotides, it is necessary for any oligonucleotide to undergo a costly and time-intensive development process, particularly in the case of production on a relatively large scale. The associated costs increase linearly with the number of oligonucleotides needed in the assay. For each target sequence to be detected, a respective oligonucleotide modified with an appropriate fluorescent dye is used. This can make it necessary to use many oligonucleotides, sometimes well over 25, depending on the microorganism to be detected. Experimental screening for new or better oligonucleotide variants comprising in each case at least one modification with fluorescent dye is accordingly very costly, since each variant needs to be modified with a fluorescent dye. The advantage here is that an easy and cost-efficient analysis can be achieved that is able to ensure the simultaneous determination of a plurality of target sequences in one assay.

SUMMARY

Against this background, it is an object of the present invention to provide an oligonucleotide probe combination for the specific detection of target sequences, i.e. DNA sequences or RNA sequences in microorganisms, that enables specific detection of a plurality of different target sequences in a FISH method that can be executed cost-efficiently and outside a laboratory setting.

The invention achieves this object through one or more of the features disclosed herein.

More particularly, in order for the invention to achieve said object with an oligonucleotide probe combination of the type described in the introduction, it is thus proposed that at least one functional section and at least one detectable tag, in particular a color tag, be used, wherein the at least one functional section binds specifically to the target sequence of microorganisms of the group to be detected and triggers a detectable signal through an interaction with the at least one tag. The oligonucleotide probe combination of the invention includes at least one primary probe and at least one secondary probe that are linked to one another, preferably via complementary base pairs, but constitute separate chains, wherein the at least one primary probe is formed with the at least one functional section and the at least one secondary probe is formed with the at least one tag. Standardization of the labeling process, in particular of the labeling with color tags, is consequently easily achievable, since it is possible for the same sequence always to be used as the secondary probe. The advantage here is that this allows the ability to detect microorganisms to be significantly improved since, with the combination of a plurality of oligonucleotide probes, it is possible to achieve a higher intensity of fluorescence per bacterium by virtue of the ability to detect a plurality of target sequences at the same time.

Advantageous refinements of the invention are described below, which alone or in combination with the features of other refinements may optionally be combined together with the features noted above.

In an advantageous embodiment of the invention, the at least one primary probe is designed in the form of a linear probe. Examples include mono-labeled probes, dual-labeled probes, tetra-labeled probes and multi-labeled probes. Alternatively or additionally, the primary probe may be designed in the form of a probe having secondary structure, preferably a hairpin probe. Examples include molecular beacons and Scorpions probes. What is achievable as a result is a higher fluorescence intensity and also a better signal-to-noise ratio, which is advantageous especially for an automated application.

In an advantageous embodiment of the invention, the at least one primary probe has a stem section that is designed for the formation of the hairpin structure. The invention utilizes here the ability of the stem-forming nucleotides to form, in the absence of target sequences, a "hairpin" structure, as a result of which a signal from the tag, such as the fluorescence of a dye, is suppressed. The signal from the tag can for example be suppressed in the presence of a quencher molecule. After binding of the functional section to the target sequence, this "hairpin" structure breaks down again, whereupon it is possible to detect the signal from the tag, in particular the fluorescence of the dye, which is no longer being suppressed.

In an advantageous embodiment of the invention, the at least one primary probe has at least one bait section that is formed in correspondence with the stem section or separately, in particular spaced apart, from the stem section. This allows a flexible arrangement in the length of bait section sequence to be achieved, that can be adapted or optimized to the sequence of the secondary probe.

In an advantageous embodiment of the invention, the bait section is formed on at least one end of the at least one primary probe. This makes it possible for there to be at least one binding site for the secondary probe labeled with a tag. Alternatively, the bait section can be formed at both ends of the at least one primary probe. This allows signal amplification and a higher intensity of fluorescence to be achieved, since binding of two secondary probes to a primary probe can be enabled. When two bait sections are present in each primary probe, it is advantageous when two secondary probes each having two color tags, for example fluorescent tags, are able to bind. This allows a plurality of color tags per target sequence to be used. In addition, by forming a bait section at one or both ends of the primary probe rather than for example in the middle of the probe, it is possible to achieve better stability of the oligonucleotide probe.

In an advantageous embodiment of the invention, the at least one primary probe has a quencher (signal quencher, in particular fluorescence quencher) designed for deactivation of the tag of the secondary probe. The advantage here is that no fluorescence signals are emitted by oligonucleotide probes that are not bound to a target sequence. This allows an improved signal-to-noise ratio to be achieved.

In an advantageous embodiment of the invention, the at least one primary probe includes a bait section to which the secondary probe binds. In particular, the at least one primary probe may include at least one modified nucleotide. The modifications may relate to the sugar residues of the nucleotides (for example attachment of fluorescent groups, heavy metal ions or amino linkers, the bases (for example thiobase analogs, fluorescent groups, unusual bases) or the phosphate residues (for example non-hydrolyzable derivatives, photolabile groups). The modified nucleotides are preferably so-called "locked nucleid acids" (LNA) nucleotides. The LNA structural units should not be self-complementary. Through the incorporation of one or more modified nucleotides, for example LNA nucleotides, it is possible to increase the binding affinity of the oligonucleotide probe. The advantage here is that the increased binding affinity shortens the length of the oligonucleotide probe and thus allows a more cost-efficient oligonucleotide probe to be provided.

In an advantageous embodiment of the invention, the secondary probe consists of DNA nucleotides or of a mixture of DNA nucleotides and at least one modified nucleotide. The at least one modified nucleotide is preferably an LNA nucleotide. The advantage here is that the modified nucleotides, in particular LNA nucleotides, are able to strengthen the complementary base pairing between the secondary probe and the bait section of the primary probe, resulting in the formation of more stable dimers that enable a better signal. In addition, the at least one modified nucleotide of the secondary probe and the at least one modified nucleotide of the primary probe are formed such that they are not complementary to one another.

In an advantageous embodiment of the invention, the secondary probe has a length of fewer than 25 nucleobases. This allows overly strong binding behavior to be avoided and makes it possible to provide a more cost-efficient oligonucleotide probe having better diffusion properties.

In an advantageous embodiment of the invention, the at least one tag includes one label. Alternatively, the tag may include a combination of at least two labels. It is possible for the label to include a fluorescence-based, biotin-labeled and/or radiolabeled tag. Optical detection is therefore achievable. Alternatively or additionally, the label may include an affinity label and/or an enzymatically active group. The affinity label may for example include biotin-streptavidin or antigen-antibody affinity binding pairs.

It is also possible for the tag to include a constituent selected from peroxidase, preferably horseradish peroxidase, and/or phosphatase, preferably alkaline phosphatase.

In an advantageous embodiment of the invention, the at least one target sequence includes one or more different DNA sequence(s) and/or RNA sequence(s). Specific detection of microorganisms at the DNA and/or RNA level can thus be enabled.

The invention further provides a method for the specific detection of microorganisms in a sample by means of in-situ hybridization (ISH), in particular fluorescence in-situ hybridization (FISH), comprising the following steps: a) permeabilization and fixation of the microorganisms present in the sample; b) incubating the fixed microorganisms with at least one oligonucleotide probe combination, in particular as described above and/or as claimed in one of the claims directed to an oligonucleotide probe combination, wherein the individual oligonucleotide probe combination undergoes complementary hybridization with a plurality of different nucleic acids of the microorganisms; c) preferably optically detecting the hybridizations generated in the individual microorganisms. Optical detection can be by fluorescence measurement or by for example luciferase measurement, preferably Renilla-luciferin-2-monooxygenase.

It is possible for optical detection of the generated hybridizations to be preceded by the additional performance of a wash step. This allows unhybridized nucleic acid probes to be removed, thus enabling an improved signal-to-noise ratio.

Furthermore, in an advantageous embodiment of the invention, the detection includes a step of quantification with hybridized oligonucleotide probes. In addition to a qualitative statement, this makes it possible also to achieve absolute quantification of the microorganisms to be detected, for example on the basis of a particle measurement.

Furthermore, in an advantageous embodiment of the invention, each oligonucleotide probe combination binds detectably only to the complementary target sequences. This makes it possible to achieve high specific detectability for the desired microorganisms.

A preferred application provides a use of at least one oligonucleotide probe combination, in particular as described above and/or as claimed in one of the claims directed to an oligonucleotide probe combination, for the specific detection of a plurality of different nucleic acid sequences, in particular wherein detection takes place in a natural sample selected from clinical samples, samples of foodstuffs, samples of surroundings, environmental samples, veterinary diagnostics samples or in a laboratory culture. The advantage here is that specific detection of microorganisms can be made possible in different fields of application.

A preferred application provides a use of a sample carrier, in particular as described above and/or as claimed in one of the claims directed to a method and/or as claimed in one of the claims directed to a use.

The sample carrier of the invention can be designed as a disk-shaped sample carrier. For example, the sample carrier can be designed as a planar sample carrier. The advantage here is that the disk shape of the sample carrier can utilize centrifugal force for fluid conveyance. Fluid conveyance is also achievable by means of pressure or in another way. The sample carrier can alternatively have a three-dimensional extent, for example in the form of a cylinder or in the style of a cuvette.

For example, the disk-shaped nature can have rotational symmetry. This can be advantageous for centrifugation. It is also alternatively possible to form rectangular sample carriers, as in the case of a chip card, or segment-shaped sample carriers, as in the case of a pizza slice.

For example, in the method of the invention it is possible for permeabilization, fixation and/or hybridization and/or detection of the tag to take place in the sample carrier.

BRIEF DESCRIPTION OF THE DRAWINGS

The invention will now be described in more detail with reference to exemplary embodiments, but without being limited to said exemplary embodiments. Further exemplary embodiments arise through combining the features of one or more claims with one another and/or with individual or multiple features of the exemplary embodiments.

In the figure(s):

FIG. 1 shows a schematic diagram of a first embodiment variant of an oligonucleotide probe combination of the invention having a primary probe designed in the form of a linear primary probe and a secondary probe designed in the form of a linear secondary probe, which are linked to one another via complementary base pairs, wherein the primary probe has a single bait section and the secondary probe is labeled with two tags, FIG. 2 shows a further schematic diagram of a second embodiment variant of an oligonucleotide probe combination of the invention having a primary probe designed in the form of a linear primary probe and a secondary probe designed in the form of a linear secondary probe, which are linked to one another via complementary base pairs, wherein the primary probe has two bait sections and the secondary probe is labeled with two tags, FIG. 3 shows a further schematic diagram of a third embodiment variant of an oligonucleotide probe combination of the invention having a primary probe designed in the form of a hairpin primary probe having an internal hairpin structure and a secondary probe designed in the form of a linear secondary probe, which are linked to one another via complementary base pairs, wherein the primary probe has a single bait section and the secondary probe is labeled with two tags, FIG. 4 shows a further schematic diagram of a fourth embodiment variant of an oligonucleotide probe combination of the invention having a primary probe designed in the form of a hairpin primary probe having an internal hairpin structure and a secondary probe designed in the form of a linear secondary probe, which are linked to one another via complementary base pairs, wherein the primary probe has a single bait section and a quencher, and wherein the secondary probe is labeled with two tags, FIG. 7 shows some examples for secondary probes 6, as follows: SQ1 (SEQ ID NO: 1), SQ1L (SEQ ID NO: 2), SQ2 (SEQ ID NO: 3), SQ3 (SEQ ID NO: 4), SQ4 (SEQ ID NO: 5), SQ4L (SEQ ID NO: 6), SQ5 (SEQ ID NO: 7), SQ6 (SEQ ID NO: 8), SQ7 (SEQ ID NO: 9), and SQ8 (SEQ ID NO: 10), and FIG. 8 shows some examples for primary probes 5, as follows: primary nucleic acid probe Q162-3' with internal hairpin (SEQ ID NO: 11), primary nucleic acid probe with internal hairpin and bait 5' and 3' (SEQ ID NO: 12), primary nucleic acid probe L162-3' (linear probe) (SEQ ID NO: 13), and primary nucleic acid probe RL162 (linear probe at 5' and 3') (SEQ ID NO: 14).

DETAILED DESCRIPTION

Figure 5:
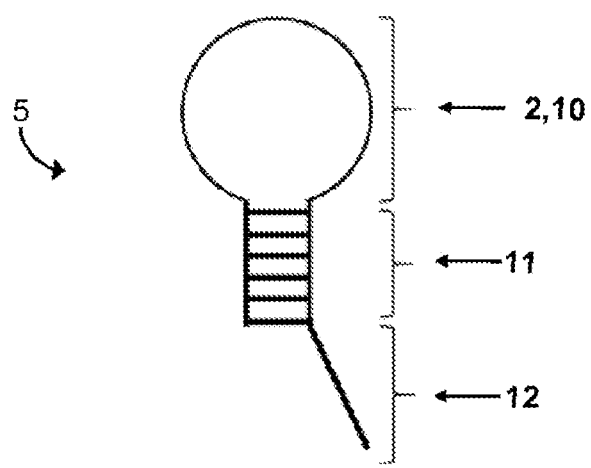
FIG. 5 shows a schematic diagram of a primary probe having an internal hairpin structure and a single bait section.

FIGS. 1 to 4 show four possible exemplary embodiments of an oligonucleotide probe combination of the invention in simplified schematic form, where 1 in each case refers to the oligonucleotide probe combination in its entirety.

The oligonucleotide probe combination 1 is designed for the execution of a detection method for the identification of particular microorganisms. In this method, the oligonucleotide probe combination 1 binds specifically via a functional section 2 (functional sequence) to a preferably complementary target sequence of the microorganism to be detected.

In order for detection to be possible, the oligonucleotide probe combination 1 is labeled with at least one detectable tag 3. Optical detection may here be enabled by for example a color tag 4.

The oligonucleotide probe combination 1 includes at least one primary probe 5 and at least one secondary probe 6 that have different functions, as elucidated in more detail hereinbelow. The term "probe" may for the purposes of the invention refer to an oligonucleotide.

The abovementioned tag 3 generates a detectable signal preferably only when specific binding of the functional section 2 to the target sequence has occurred. As a result of this binding, an interaction between the primary probe 5 and the secondary probe 6 is able to trigger a detectable signal from the tag 3. The signal may for example be an optically detectable signal such as a color reaction.

In order to be able to detect specific binding of the oligonucleotide probe combination 1 to a target sequence, the primary probe 5 and the secondary probe 6 must be linked to one another. The linking may here be established for example via complementary base pairs 7 of the components 5 and 6 that are in each case produced in the form of a chain 8.

The primary probe 5 includes the abovementioned functional section 2 that binds to the target sequence of the microorganism. The primary probe 5 may for example be designed to allow the detection of rRNA sequences specific for the bacterial family "Enterobacteriaceae".

The primary probe 5 designed in the form of an oligonucleotide may for example have the following construction. It comprises a section of nucleic acid sequence (functional section 2) that is reverse-complementary to a nucleic acid of the target sequence to be detected in a microorganism. Under the given assay conditions (i.e. adequately high melting temperature), these bind to one another. Under the given assay conditions, the primary probe 5 does not undergo binding in closely related microorganisms that are not intended to be detected (preferably at least 2 mismatches). It comprises a second section of sequence (bait section 12) that is reverse-complementary to a section of nucleic acid sequence in the secondary probe 6. Under the given assay conditions (i.e. adequately high melting temperature), these bind to one another. This section of sequence (bait section 12) does not bind in the target sequence. This bait section may be present at 3' and/or at the 5' end of the primary probe 5. The "bait section" can be spaced apart from the remainder of the probe (first section of sequence), particularly from functional section 2, by a "linker" made up of one or more nucleotides. The second section of sequence (bait section 12) can be formed such that it has no complementarity within the primary probe longer than five bases in succession.

The secondary probe 6 designed in the form of an oligonucleotide includes the at least one tag 3 mentioned above, through which it is possible to generate a detectable signal. The secondary probe 6 has the properties that it comprises a section of nucleic acid sequence that is reverse-complementary to the corresponding section of nucleic acid sequence (bait section 12) in the primary probe 5. The chosen melting temperature of the secondary probe 6 is such that, under the given assay conditions, the latter undergoes hybridization with the complementary section of the primary probe 5. This melting temperature is the same or higher than that for the hybrid of the primary probe having the target sequence of the microorganism. The secondary probe 6 can have a maximum of 25 bases. Under the given assay conditions, the secondary probe 6 does not undergo binding in one of the target sequences, to other sites in the microorganism, and/or to the reverse complement thereof (preferably at least 2 mismatches present). The secondary probe 6 is composed of a sequence of a maximum of three of the four possible bases (G,T,C,A). The bases G and C are not used in the same sequence (i.e. either/or). The secondary probe 6 can be exclusively constructed of the bases A and G (heteropurine sequence), with a plurality of alternating repeats of 2 to 5 of the same bases (e.g. AAGGAAGGAA (SEQ ID NO: 16)), since this results in a strongly reduced affinity for RNA sequences, thus reducing the "off-target" risk (risk of false positives). The sequence of the secondary probe 6 can be formed such that there is no self-complementarity of more than 4 bases in succession. One or more nucleotides of the secondary probe 6 may be formed as modified nucleotides for the purposes of higher binding affinity and/or higher melting temperature and/or shortening of the probe length. The modifications may relate to the sugar residues of the nucleotides, the bases or the phosphate residues. The modified nucleotides are preferably so-called "locked nucleic acids" (LNA) nucleotides. The LNA structural units should not be self-complementary.

FIG. 7 shows examples for secondary probe 6, with LNAs doubly underlined. FIG. 8 shows some examples for primary probe 5. The entire sequence consists of reverse-complementary section of the target sequence (upper-case letters), the bait sequence (doubly underlined upper-case letters), and the stem sequences (lower-case letters) or a linker nucleotide (doubly underlined lower-case letters).

The use of a secondary probe 6 makes it possible to reduce the number of production development processes necessary for label-modified oligonucleotides to a single production process. It also makes it possible to simplify screening for appropriate target sequences. For example, the simultaneous detection of a plurality of target sequences is simplified, which for example significantly increases the ability to detect bacteria such as Enterobacteriaceae, since it is possible to achieve a higher signal intensity, such as intensity of fluorescence, per bacterium (i.e. better signal-to-noise ratio).

The at least one tag 3 can include a label or a combination of at least two labels from the group of fluorescence-based, biotin-labeled or radiolabeled tags, an affinity label, and/or an enzymatically active group. The primary probe 5 can alternatively or additionally be 5' or 3' end-conjugated with a dye or quencher 13, as shown in FIG. 4.

FIGS. 1 and 2 show a primary probe 5 that is designed in the form of a linear probe 9, since the individual nucleobases 14 of the primary probe 5 are not linked to one another, that is to say not bound to other nucleobases 14 of the primary probe 5, and because of their sequence order cannot form any internal secondary structures.

Figure 6:
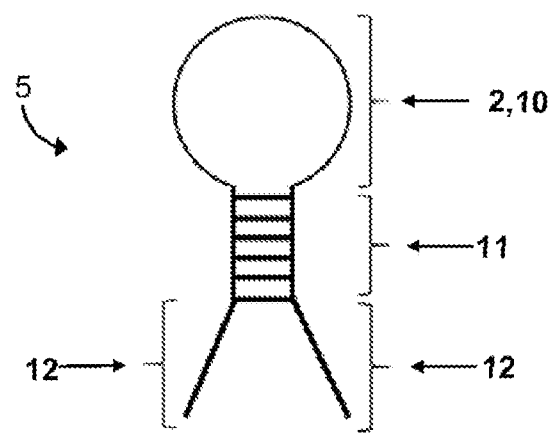
FIG. 6 shows a further schematic diagram of a primary probe having an internal hairpin structure and two bait sections.

FIGS. 3-6 show a further embodiment variant of a primary probe 5 that is designed in the form of a hairpin probe 10 (hairpin primary probe). The hairpin probe 10 has a stem section 11 in which nucleobases 14 of the primary probe 5 are bound to one another, with the result that the functional section 2 forms the loop of a hairpin structure 10.

The primary probe 5 formed as a hairpin probe comprises two complementary sections of nucleic acid sequence (in particular 5 to 8 bases in length) that bind to one another under the given assay conditions, thereby enabling a hairpin structure. These two sections of sequence form the previously mentioned stem section 11 of the hairpin structure. This accordingly allows an internal hairpin structure to form. The chosen sequence of the bait section 12 can be such that it lies outside this hairpin structure and is not involved therewith (see FIGS. 3-6). The hairpin structure both makes it easier to distinguish mismatches and enables the additional incorporation of a quencher 13 into the primary probe.

The oligonucleotide probe combination 1 described and/or claimed herein is thus suitable in particular for use in a method for the specific detection of microorganisms in a sample by means of fluorescence in-situ hybridization (FISH) as described and/or claimed herein.

The invention thus relates in particular to an oligonucleotide probe combination 1 for the specific detection of microorganisms having a primary probe 5 and a secondary probe 6, wherein the primary probe 5 has at least one functional section 2 and the secondary probe 6 at least one tag 3 generating a detectable signal, wherein the functional section 2 binds specifically to a target sequence of a microorganism to be detected, and wherein the primary probe 5 and the secondary probe 6 are linked to one another but constitute separate chains 8.

LIST OF REFERENCE NUMBERS

1 Oligonucleotide probe combination
2 Functional section; functional sequence
3 Tag
4 Color tag
5 Primary probe
6 Secondary probe
7 Complementary base pair
8 Chain
9 Linear probe
10 Hairpin probe; hairpin structure
11 Stem section; stem sequence
12 Bait section; bait sequence
13 Quencher
14 Nucleobase

The invention claimed is:

1. An oligonucleotide probe combination for detection of microorganisms in a sample by in-situ hybridization (ISH), the oligonucleotide probe combination comprising: at least one primary probe comprising at least one functional section, a bait section, and a quencher, wherein said bait section is present at the 3' and/or at the 5' end of the at least one primary probe; and at least one secondary probe comprising at least one detectable tag that generates a detectable signal, wherein the quencher of the at least one primary probe is configured for suppression of the detectable signal of the at least one detectable tag of the at least one secondary probe, the at least one primary probe and the at least one secondary probe are separate oligonucleotide probes, the at least one primary probe is linked to the at least one secondary probe via complementary base pairing between the bait section of the at least one primary probe and the at least one secondary probe, the at least one primary probe binds to at least one target sequence of microorganisms of a group to be detected by base pairing between the at least one functional section of the at least one primary probe and the at least one target sequence of the microorganisms to be detected, and upon binding of the functional section of the at least one primary probe to the target sequence, the quencher no longer suppresses the detectable tag signal of the at least one secondary probe that is linked to the at least one primary probe such that the secondary probe is able to trigger a detectable signal from the tag.

2. The oligonucleotide probe combination as claimed in claim 1, wherein the at least one primary probe is a linear probe.

3. The oligonucleotide probe combination as claimed in claim 2, wherein the at least one primary probe is a hairpin probe having a stem section and at least one bait section that is formed separately from the stem section.

4. The oligonucleotide probe combination as claimed in claim 3, wherein the bait section is formed on at least one end of the at least one primary probe.

5. The oligonucleotide probe combination as claimed in claim 1, wherein the at least one secondary probe includes DNA nucleotides.

6. The oligonucleotide probe combination as claimed in claim 1, wherein the at least one secondary probe has a length of fewer than 25 nucleobases.

7. The oligonucleotide probe combination as claimed in claim 1, wherein the at least one detectable tag comprises a label wherein said label consists of fluorescence-based tags.

8. An oligonucleotide probe combination for detection of microorganisms in a sample by in-situ hybridization (ISH), the oligonucleotide probe combination comprising: at least one primary probe including comprising at least one functional section, a bait section, and a quencher, wherein said bait section is present at the 3' and/or at the 5' end of the at least one primary probe; and at least one secondary probe comprising at least one detectable tag that generates a detectable signal, wherein the quencher of the at least one primary probe is configured for suppression of the detectable signal of the at least one detectable tag of the at least one secondary probe, the at least one primary probe and the at least one secondary probe are separate oligonucleotide probes, the at least one primary probe is linked to the at least one secondary probe via complementary base pairing between the bait section of the at least one primary probe and the at least one secondary probe, the at least one primary probe binds to at least one target sequence of microorganisms of a group to be detected by base pairing between the at least one functional section of the at least one primary probe and the at least one target sequence of the microorganisms to be detected, and upon binding of the functional section of the at least one primary probe to the target sequence, the quencher no longer suppresses the detectable tag signal of the at least one secondary probe that is linked to the at least one primary probe such that the secondary probe is able to trigger a detectable signal from the tag and the at least one target sequence includes comprises at least one or more of different RNA sequence(s).

9. The oligonucleotide probe combination of claim 1, wherein oligonucleotide probe combination is configured for the detection of at least one target sequence of the microorganisms.

10. The oligonucleotide probe combination of claim 2, wherein the primary probe is in the form of a hairpin probe and has a stem section that is configured for formation of a hairpin structure.

\* \* \* \* \*

SEQUENCE LISTING

<160> NUMBER OF SEQ ID NOS: 16

<210> SEQ ID NO 1
<211> LENGTH: 25
<212> TYPE: DNA
<213> ORGANISM: Artificial Sequence
<220> FEATURE:
<223> OTHER INFORMATION: secondary nucleic acid probe SQ1

<400> SEQUENCE: 1
tccatccctc cctccactct ctttt                                    25

<210> SEQ ID NO 2
<211> LENGTH: 25
<212> TYPE: DNA
<213> ORGANISM: Artificial Sequence
<220> FEATURE:
<223> OTHER INFORMATION: secondary nucleic acid probe SQ1L

<400> SEQUENCE: 2
tccatccctc cctccactct ctttt                                    25

<210> SEQ ID NO 3
<211> LENGTH: 25
<212> TYPE: DNA
<213> ORGANISM: Artificial Sequence
<220> FEATURE:
<223> OTHER INFORMATION: secondary nucleic acid probe SQ2

<400> SEQUENCE: 3
ttttcctccc tccctccctc ctttt                                    25

<210> SEQ ID NO 4
<211> LENGTH: 25
<212> TYPE: DNA
<213> ORGANISM: Artificial Sequence
<220> FEATURE:
<223> OTHER INFORMATION: secondary nucleic acid probe SQ3

<400> SEQUENCE: 4
aaaaggaggg agggagggag gaaaa                                    25

<210> SEQ ID NO 5
<211> LENGTH: 20
<212> TYPE: DNA
<213> ORGANISM: Artificial Sequence
<220> FEATURE:
<223> OTHER INFORMATION: secondary nucleic acid probe SQ4

<400> SEQUENCE: 5
aaagagaggg gggagagaaa                                          20

<210> SEQ ID NO 6
<211> LENGTH: 19
<212> TYPE: DNA
<213> ORGANISM: Artificial Sequence
<220> FEATURE:
<223> OTHER INFORMATION: secondary nucleic acid probe SQ4L

<400> SEQUENCE: 6
ttttctcccc ctctctttt                                           19

<210> SEQ ID NO 7
<211> LENGTH: 16
<212> TYPE: DNA
<213> ORGANISM: Artificial Sequence

```
<220> FEATURE:
<223> OTHER INFORMATION: secondary nucleic acid probe SQ5

<400> SEQUENCE: 7 tttttcccttc cctttt                                                  16

<210> SEQ ID NO 8
<211> LENGTH: 15
<212> TYPE: DNA
<213> ORGANISM: Artificial Sequence
<220> FEATURE:
<223> OTHER INFORMATION: secondary nucleic acid probe SQ6

<400> SEQUENCE: 8
aaaagggagg gaaaa                                                    15

<210> SEQ ID NO 9
<211> LENGTH: 17
<212> TYPE: DNA
<213> ORGANISM: Artificial Sequence
<220> FEATURE:
<223> OTHER INFORMATION: secondary nucleic acid probe SQ7

<400> SEQUENCE: 9
aagggagggg gagggaa                                                  17

<210> SEQ ID NO 10
<211> LENGTH: 13
<212> TYPE: DNA
<213> ORGANISM: Artificial Sequence
<220> FEATURE:
<223> OTHER INFORMATION: secondary nucleic acid probe SQ8

<400> SEQUENCE: 10 aaggggggggg gaa                                                     13

<210> SEQ ID NO 11
<211> LENGTH: 59
<212> TYPE: DNA
<213> ORGANISM: Artificial Sequence
<220> FEATURE:
<223> OTHER INFORMATION: primary nucleic acid probe Q162-3' with
      internal hairpin

<400> SEQUENCE: 11
ccgggtccta cttcttttgc aacccactac ccggaaaagg agggagggag ggaggaaaa    59

<210> SEQ ID NO 12
<211> LENGTH: 84
<212> TYPE: DNA
<213> ORGANISM: Artificial Sequence
<220> FEATURE:
<223> OTHER INFORMATION: primary nucleic acid probe with internal
      hairpin and bait 5' and 3'

<400> SEQUENCE: 12
aaaaggaggg agggagggag gaaaaccggg tcctacttct tttgcaaccc actacccgga   60
aaaggaggga gggagggagg aaaa                                          84

<210> SEQ ID NO 13
<211> LENGTH: 47
<212> TYPE: DNA
<213> ORGANISM: Artificial Sequence
<220> FEATURE:
<223> OTHER INFORMATION: primary nucleic acid probe L162-3' (linear
      probe)
```

```
<400> SEQUENCE: 13
cctacttctt ttgcaaccca ctaaaggag ggagggaggg aggaaaa                    47

<210> SEQ ID NO 14
<211> LENGTH: 72
<212> TYPE: DNA
<213> ORGANISM: Artificial Sequence
<220> FEATURE:
<223> OTHER INFORMATION: primary nucleic acid probe RL162 (linear probe
      at 5' and 3')

<400> SEQUENCE: 14
aaaaggaggg agggagggag gaaaacctac ttcttttgca acccactaaa aggagggagg     60
gagggaggaa aa                                                        72

<210> SEQ ID NO 15
<211> LENGTH: 74
<212> TYPE: DNA
<213> ORGANISM: Artificial Sequence
<220> FEATURE:
<223> OTHER INFORMATION: primary probe RLV162 (linear probe at 5' and 3'
      with linker base)

<400> SEQUENCE: 15
aaaaggaggg agggagggag gaaaatccta cttcttttgc aacccactta aaggaggga      60 gggagggagg aaaa                                                      74

<210> SEQ ID NO 16
<211> LENGTH: 10
<212> TYPE: DNA
<213> ORGANISM: Artificial Sequence
<220> FEATURE:
<223> OTHER INFORMATION: Alterntating repeats

<400> SEQUENCE: 16
aaggaaggaa                                                           10
```